(12) United States Patent
Galtie et al.

(10) Patent No.: US 8,228,504 B2
(45) Date of Patent: Jul. 24, 2012

(54) DEVICE FOR OPTOELECTRONIC MEASUREMENT OF THE HYDRATION OF A PLANT IN ITS NATURAL ENVIRONMENT

(75) Inventors: Jean François Galtie, Cahors (FR); Marc Lescure, Toulouse (FR)

(73) Assignees: Universite de Toulouse II le Mirail, Toulouse (FR); Institut National Polytechnique de Toulouse (INPT), Toulouse (FR)

( * ) Notice: Subject to any disclaimer, the term of this patent is extended or adjusted under 35 U.S.C. 154(b) by 206 days.

(21) Appl. No.: 12/667,896

(22) PCT Filed: Jul. 1, 2008

(86) PCT No.: PCT/EP2008/058419
§ 371 (c)(1),
(2), (4) Date: Apr. 7, 2010

(87) PCT Pub. No.: WO2009/007269
PCT Pub. Date: Jan. 15, 2009

(65) Prior Publication Data
US 2010/0182604 A1    Jul. 22, 2010

(30) Foreign Application Priority Data
Jul. 6, 2007 (FR) ................... 07 04883

(51) Int. Cl.
*G01N 21/00* (2006.01)
(52) U.S. Cl. .................................. 356/432
(58) Field of Classification Search .......... None
See application file for complete search history.

(56) References Cited

U.S. PATENT DOCUMENTS

| 4,380,169 A | 4/1983 | Graham |
| 5,334,942 A | 8/1994 | Hulse et al. |

(Continued)

FOREIGN PATENT DOCUMENTS

| CA | 960 308 | 12/1974 |

(Continued)

OTHER PUBLICATIONS

Galtie et al., "Remotely based fuels water content assessment applied to operational fire risk prevision: Requirements, situations and perspective", Forest Ecology and Management, Elsevier vol. 234, Nov. 15, 2006, XP005857258, ISSN: 0378-1127, pp. 1-3.

(Continued)

*Primary Examiner* — Tu Nguyen
(74) *Attorney, Agent, or Firm* — Young & Thompson (57) ABSTRACT

An optoelectronic device for measuring the water content in a plant element and an apparatus designed to evaluate and monitor in real time the state of hydration of the plant covers. The device includes an optoelectronic probe connected to a measurement module, the probe including: i) a first light source emitting at a wavelength corresponding to a strong water absorption band; ii) optionally, a second light source emitting at a wavelength close to the first source and weakly absorbed by water; and iii) a photo receiver having a spectral response that corresponds to the emission bands of the first light source or of the first and second light sources, the device including elements for modulating the average optical power emitted by the light source or sources at a defined frequency, and elements for synchronously detecting the light received by the photoreceiver.

20 Claims, 5 Drawing Sheets

U.S. PATENT DOCUMENTS 7,304,724 B2 * 12/2007 Durkin et al. .................. 356/73
2004/0233448 A1 11/2004 Goulas et al.

FOREIGN PATENT DOCUMENTS

| | | |
|---|---|---|
| DE | 101 48 748 | 4/2003 |
| FR | 2753272 | 3/1998 |
| FR | 2 830 325 | 4/2003 |
| FR | 2894769 A1 | 6/2007 |
| JP | 1049939 | 2/1986 |
| JP | 1049937 | 2/1989 |
| JP | 1049940 | 2/1989 |
| JP | 5-313898 | 11/1993 |
| JP | 2005-308733 | 11/2005 |
| WO | 83/02326 | 7/1983 |
| WO | 03/006960 | 1/2003 |

OTHER PUBLICATIONS

International Search Report dated Sep. 8, 2008, from corresponding PCT application.
International Preliminary Report on Patentability in PCT/EP2008/067069, Aug. 9, 2008.

* cited by examiner

DEVICE FOR OPTOELECTRONIC MEASUREMENT OF THE HYDRATION OF A PLANT IN ITS NATURAL ENVIRONMENT

BACKGROUND OF THE INVENTION

This invention belongs to the field of the evaluation and the tracking of the state of hydration of plant covers, and more particularly to methods that rely on the measurement of the hydric state of plant samples by optoelectronic techniques.

It has as its object a terrain optoelectronic device that makes it possible to measure the water content in a plant without impairing or destroying it, as well as an apparatus that is designed to evaluate and to track its hydric status in real time. It also has as its object a process that implements said device and said apparatus, in particular for the monitoring in real time of the state of hydration of an extensive plant cover.

DESCRIPTION OF THE PRIOR ART

The water content of the plant covers varies over time under the combined action of physiological regulation mechanisms and mesological factors. These variations exert a direct and gradual influence on the production level and the vulnerability of plants. The knowledge of the period of occurrence, the intensity, and the duration of hydric deficiencies therefore constitutes an indispensable stage for anticipating the effects of periods of dryness on crops or else for evaluating the risks of fire to a forest zone, scrub, or fallow land. The measurement of the hydration level is an essential parameter that is taken into account in predictive methods for the purpose of automatically controlling irrigation operations before the shortage of water becomes critical or at least for indicating in warning form, for example, this water shortage. The importance of these forecasts is measured when it is known that the dryness is the essential cause of numerous forest fires and enormous losses of crops.

Different methods for detection and tracking, direct or indirect, have been used. Traditional agro-meteorological methods are known, based on the extrapolation of environmental measurements such as temperature, moisture in the air and of the ground, the intensity of radiation, precipitation or wind. More recently, remote detection has been developed for purposes of cartography and agricultural monitoring. Today, these technologies offer the possibility of studying land quickly and reliably using the combination of satellite imagery with computer science and with geographical computer systems. However, they provide an overall assessment for the land surface but do not provide the critical points that make it possible to take into account the nature of plants, the types of soil, and the contours. It is also quite obvious that the deployment of such means is only justified economically on a large scale, in particular for meeting objectives for land settlement.

Methods that are better suited for specific and targeted measurements are also widely used. It is possible to cite techniques that are based on the measurement of conductivity of plant leaves, such as in U.S. Pat. No. 5,334,942 or FR 2 753 272. For example, FR 2 753 272 describes a sensor of the presence of a liquid on a leaf using a detector that comprises two electrodes that are connected to an electronic circuit. Also, according to WO83/02326, a process is known that uses the retrodiffusion of the infrared radiation that is emitted by a source inside the material that is to be examined. The publications CA 960 308 or JP 5 313 898 describe equipment for measuring moisture by absorption of microwaves.

Photometric methods are also used in the laboratory. For example, JP2005 308 733 describes a method for evaluating hydric stress that consists in calculating spectral reflectance from differences of light intensity, reflected and absorbed by a leaf and a white panel. Solutions based on the selective absorption of the water content in the near-infrared have been proposed. However, they require the implementation of devices equipped with collimation optics and/or with relatively complex integration systems to obtain a satisfactory signal-to-noise ratio and precision.

In general, all of these methods have the drawback of being poorly suited to the production of measurements of the terrain because of the fragility of the equipment or the complexity of implementing the measurements. The majority involve the destruction of the plant material with each measurement, which prevents tracking on homogeneous material and are also produced in a controlled light environment that cannot be reproduced in nature.

It therefore appeared to be a major issue—in order to ensure an effective and long-lasting management of the agricultural and forestry resource—to use a system for direct and instantaneous measurement in situ of the hydration of the plant cover.

SUMMARY OF THE PRESENT INVENTION

The object of this invention is to propose a device and a process that implement said device for the direct, non-destructive and instantaneous measurement of the hydration level of a plant. Another object of the invention is to provide a means for measurement in vivo and in situ, which is not affected by environmental conditions, in particular by the light from the sun. It also has the object of proposing a tracking method that makes it possible to continuously monitor the changes in the hydric status of a plant cover. Another object of this invention is to obtain information in real time on one or more determined plant zones that can be removed from one another. Another object of the invention is to use a method in which the measuring is automated, as well as preferably also the control of the device and the processing of the result of the measurements. Finally, a small device that is sturdy, in particular with regard to unfavorable, and even hostile, weather conditions, independent in energy and data processing, and not very expensive, is sought.

These objectives are achieved using the device that is the object of the invention, comprising an integrated optical circuit that, by using the optical properties of the leaves in the infrared means, issues instantaneous and precise quantitative data on the hydration level of a leaf sample. Actually, whereby the fraction of transmitted light is directly connected to the fraction that is absorbed by the water that is contained in the leaf—the greater the water content, the larger the absorbed fraction and the smaller the transmitted fraction—the measured size is thus significantly connected to the water content of the leaf. This information, collected from one or more remote-controlled sensors that are carefully implanted in the natural space, can supply models of behavior and tracking of plant covers subjected to a hydric constraint for the purpose of establishing rapid and operational forecasts. Such a system also makes it possible to take into account the local physical and meteorological conditions.

It thus provides a functional response to the primary technical, operating and economical constraints that are identified. Its innovative nature sticks to the measuring process that ensures indifference to the generally detrimental environmental conditions, such as ambient lighting or temperature, and which makes possible an automatic production of taking successive measurements without impairing the sample. It also sticks to the fact that the device constitutes an efficient land instrument that is integrated, miniaturized and portable, with a low relative cost. All of these characteristics contribute to making possible successive measurements on a sample in situ, thus opening the way to an efficient tracking in space and over time from one or more apparatuses that are installed on stationary sites or in a network.

"Plant element" or "sample" is defined as a portion of a plant whose water content is characteristic of the hydric status of the entire plant and whose slight thickness is suitable for an optical transmittance measurement. It is generally a leaf. The plant can be a cultivated kind when an agricultural zone is monitored or most often wild for the prevention of fires. The element or sample preferably has an enduring nature at least for the duration of the monitoring period.

More specifically, this invention has as its object a device for determining the rate of hydration of a plant element in its natural environment, comprising an optoelectronic probe that can take a measurement of the optical transmission coefficient, combined with a measuring box, whereby the probe comprises:
  i) A first light source that emits at a wavelength that corresponds to a band of high water absorption,
  ii) Optionally a second light source that emits at a wavelength that is close to the first source and slightly absorbed by water, and
  iii) A photoreceptor whose spectral response corresponds to emission bands of the first and second light sources, whereby the device comprises means for modulation of the mean optical power emitted by the light source(s) according to a determined frequency and means for synchronous detection of the light that is received by the photoreceptor, such that the light that provides the relevant information that passes through the plant element and that is received by the photoreceptor is an alternating component of the light that is emitted by the light source(s).

The device thus eliminates the substantial component of the photoelectric current that is generated by the ambient light. However, the average illumination that is generated by the sun, directly or in diffuse light, and the radiation of the black body type that is emitted by the soil and the hot materials, generate a very strong mean component of the photoelectric current of the photoreceptor, which can be $10^3$ to $10^4$ larger than that obtained from sources. According to the invention, only the relevant information that is contained in the alternating component of the emitted light(s) that passed through the plant is received by the photoreceptor and is amplified by the measuring chain.

The use of a second light source is optional, but always improves the measuring. By emitting at a wavelength that is close to the first but slightly absorbed by water, it makes it possible to have a value for the transmittance of the plant element that is independent of its water content, and by comparison to access the contribution of the water content alone to transmittance.

The measuring box is dedicated to containing electronic components for signal processing, whereby the sample contains electronic detection components in addition to the photoelectric components already mentioned. This distribution is not rigid, however, and certain components can be taken away, whereby the circuits form operational modules, and the modules themselves can be designed and arranged in various ways by one skilled in the art based on specifications that are adopted. In general, the structure of the sensor can differ according to the operating mode—automatic or manual—that is implemented or according to integrated functions. The different embodiments that derive therefrom constitute variants that are obvious to one skilled in the art, which are included within the scope of this invention.

The first light source emits in a spectral interval that corresponds to one of the bands of high water absorption. A source whose spectrum is centered on 1,940 nm is advantageously used. A source that is centered toward 1,450 nm can also be used, in particular for plants with a high water content. The second source that is optionally used as a calibration means can be centered on, for example, 1,300 nm. The modulation of the mean optical power emitted by the light source(s) is carried out at a determined frequency, fixed or variable.

According to the invention, the device comprises, on the one hand, means for amplification of the alternating component of the photoelectric signal, tuned to the modulation frequency (or to a multiple frequency) of the light source(s), and, on the other hand, means for synchronous detection of said signal. For this purpose, it is possible to use a narrow-band filter that makes it possible to reduce the noise signals outside of the passband of the relevant signal and also to adjust the dephasing of the pre-amplification chain so that the photoelectric signal and the reference signal are in phase (or in phase opposition) at the input of the synchronous detector. The synchronous detection carries out the rectification of the alternating signal to provide a continuous signal whose mean value is proportional to the amplitude of the photoelectric signal. A continuous signal that is proportional to the optical power that passes through the plant element is then obtained.

According to another solution that is more modern in its design, a portion of the analog chain can be replaced by a digital-to-analog converter (DAC) combined with a digital signal processor (or DSP). After pre-amplification, the photoelectric alternating signal is digitized as well as the reference signal, whereby the two signals are coherent with the one that is obtained from a clock. The digital processing reconstitutes the basis (or a harmonic) of the photoelectric signal. Using the presence of the reference signal inside the DSP, it is easy to eliminate the non-coherent signals (noises) and to reduce the contribution of diaphony. The relevant information is deduced in digital form by the determination of the effective value (or RMS) of the digitally-filtered photoelectric signal.

According to a preferred embodiment of the device according to the invention, the probe comprises means for thermal regulation that can keep constant the temperature of the junction of the first light source and preferably also that of the photoreceptor. It is actually preferable to stabilize the light source in temperature to perfectly tune the emission spectrum to the absorption line of water. Furthermore, it is advantageous that the temperature of the photoreceptor be relatively low during heatwaves to reduce the darkness current and to adjust the longest cutoff wavelength of the spectral response.

According to the invention, the light source(s) can be, for example, electroluminescent diodes (LED), single-strip laser diodes, or surface-emission laser diodes. The photoreceptor is selected in a known manner by one skilled in the art. This is, for example, a photoconductor, or preferably a heterojunction photodiode. The photodiode is characterized by very high linearity dynamics. As a result, the low amplitude of the alternating current that contains the relevant information is superposed with neither significant deformation nor significant compression on the very high mean component generated by the ambient light. Furthermore, the photoreceptor can be combined with a transimpedance circuit that can maintain its constant polarization voltage, so that said photoreceptor preserves a linear regime.

So as to improve the precision of the measurement, it is advantageous that the light source(s) illuminate(s) a relatively large surface area of the leaf. The transmission of a fraction of the diffuse light, which radiates from the plant element according to Lambert's Law (extended source), is then picked up by the photoreceptor that has a large field of vision, which makes it possible to take into account the defects and irregularities of the plant element by achieving a mean over a large surface area. In so doing, it is necessary that the plant element be illuminated in the same manner over the entire zone.

This is why, according to an advantageous characteristic of the invention, the device comprises an optical assembly that can ensure a broad uniform illumination of the plant element by the light source(s). It is possible, for example, to have recourse to a set of prisms (or mirrors) whose reflective surface forms a 45-degree angle with the incident ray and the lenses, placed onto both sides of the plant element for orienting the light that is emitted by the first source and focusing it on the photoreceptor along a short optical passage inside a compact device.

It is also desired that the assembly have the smallest dimensions possible, compatible with its integration into a portable measuring device, without, however, the precision of Patisse measurement. For this purpose, it is wise to use an assembly that comprises two Fresnel prisms that are placed on both sides of the plant element. In this case, the reflective surface is not a flat surface at 45 degrees but comprises a number of facets arranged in stair steps, each at an angle of 45 degrees relative to the incident ray. Whereby the thickness of the prisms is thus reduced, an optical assembly is miniaturized in thickness, producing an illumination of the plant by a collimated light over a broad zone.

In a particularly advantageous variant embodiment of the device according to the invention, the probe is carried by a moving element that comprises two jaws. One of the jaws supports the light source(s) and the other jaw supports the photoreceptor, whereby said jaws are separated by a gap such that the light source(s) and the photoreceptor are placed on both sides of the plant element when a measurement is taken. The sample is thus engaged without a compressive contact between the two jaws. The optical components are at a fixed determined distance from one another during the measurements.

In a preferred embodiment, when the device according to the invention is in a measuring position, the photoreceptor is placed on the upper jaw in such a way as to limit direct solar illumination, and the light source(s) are placed on the lower jaw emitting their light flow upward. The emission and detection elements can be protected from foreign bodies (dust, water, . . . ) by protective plates that are transparent to the wavelengths under consideration. The addition of removable protective skirts made of opaque flexible plastic also makes it possible to limit the contributions to the signal of the external illumination.

According to an advantageous variant of the invention, the jaws are equipped with a joint that allows their opening. This arrangement has a significant advantage when a succession of measurements is taken on a plant element by a moving element, automated or manual. The probe can then be placed at the plant element with a maximum opening of the jaws, whereby the latter are then tightened in a measuring position. The neutral position (at rest) of the jaws can be the preferred closed position in automatic mode, or the preferred open position in manual mode. The holding in neutral position can be ensured by a draw spring or flat springs according to the selected mode.

In all of the cases, it is advantageous that the device comprise an adjustable stop that works with the jaws to adjust the opening of the latter in an optimal measurement position. A satisfactory gap is, for example, close to 5 mm to 25 mm. When it is desired to produce illumination over a large zone of the plant element, a significant gap of at least 10 mm is preferred.

When a device that is equipped with a moving element is used, the latter advantageously also comprises electrical connecting means with the measuring box, as well as electronic detection means that are combined with the photoreceptor and means for thermal regulation at least of the first light source and preferably also of the photoreceptor. The electrical cabling of the elements is conveniently included in the corresponding jaw.

An apparatus for monitoring the state of hydration of a plant element that integrates the measuring device as it was just described and able to ensure other complementary functions concurrent with the achievement of the desired result over a larger scale of time and/or space is also the object of this invention. Thus claimed is an apparatus for monitoring the state of hydration of a plant element that comprises:

A device as described above, able to carry out successive measurements of the optical transmission coefficient of a plant element in its natural environment, Means for holding the plant element in a non-restrictive position, Means for communicating with a control module.

The control module constitutes a central unit that is the master assembly including in particular the motherboard and the batteries and can be located locally in the apparatus or partially remotely, according to a structure that is suitable for the operation of the apparatus that is the object of the invention and designed according to the rules of the art known to one skilled in the art.

The means for keeping the plant element in a non-restrictive position can be of any type, provided that they make it possible to take repeated measurements on the same material at intervals. This involves, on the one hand, that the plant material be preserved in good condition during the entire monitoring run, and, on the other hand, that it preserves an identical positioning relative to the measuring element. However, it is well understood that under open field conditions, the plant is not immobile; it changes size in growing and moves in the wind. Non-restrictive position is defined as the selected holding means ensuring keeping the plant in a given position without damaging it, altering it, or, on a stronger basis, destroying it, therefore without generating stress that can modify the hydric status of the plant element. According to one characteristic of the invention, the means for holding the plant element can consist of a portico that is placed at the top of the probe, and at least one strap for immobilizing a portion of the plant that bears said plant element. Such a part is, for example, a stem or a branch on which the plant element grows and that has a rigidity that allows an immobile hold, i.e., firm but without pressure.

According to another characteristic of the invention, the apparatus can comprise an internal housing for protection of the moving element and means for moving said element up to the plant element before taking a measurement. It is thus possible between taking two measurements to shelter the components of the probe from inclement weather and dust, whereby the leaf under test remains subjected to normal conditions of sunshine or rain. According to a particular variant of the invention, the apparatus comprises an automatic mechanism for moving the probe and for controlling the movement of the jaws.

The apparatus according to the invention preferably also comprises data acquisition means relative to the climatic and/or geographic environment of the plant element. It can comprise, for example, an offloaded unit that includes a pluviometer, a thermo-hygrometer and an anemometer. In one preferred embodiment of the apparatus according to the invention, the latter comprises one or more of the following modules:

A microcontroller module for controlling electronic functions and mechanical automatic devices, A communication interface module, equipped with a local output and/or a remote output, An automatic module of the moving element, A supply module comprising an independent energy source.

Suitable electronic circuits, designed according to the rules of the art, are combined with these modules. They comprise in particular necessary cards and electronic components, in particular detection components that can be offloaded into the moving measurement element, electronics for temperature regulation, electronics of the emission block and clock, amplification, filtering and detection, a probe card, the primary analog card that ensures the link between the probe card and monitoring/measuring signals.

The device and the apparatus as they have just been described are particularly suitable for the implementation of a process for determining the hydration rate of a plant element in its natural environment. A process is thus claimed according to which a measurement of the optical transmission coefficient is carried out using a device or an apparatus according to the invention.

A process for determining the hydration rate of a plant element in its natural environment by measuring the optical transmission coefficient using an optoelectronic probe is also the object of this invention, and said process essentially comprises the stages consisting in:

Emitting light from a first source at a wavelength that corresponds to a band of high water absorption and optionally from a second source that emits at a wavelength that is close to the first and slightly absorbed by water for allowing the calibration of the optical transmittance measurement, Modulating the light that is emitted by the source(s) according to a determined frequency for obtaining an alternating component of said light, Irradiating the plant element with said alternating component of the emitted light, And receiving said alternating component of the light that has passed through the plant element on a photoreceptor and carrying out a synchronous detection of the photoelectric signal.

In the automatic configuration, the apparatus is implanted in the country close to the reference plant. The selected implantation is advantageously such that it makes it possible to perform successive measurements independently and automatically for a more or less long period, able to go up to several months. The use of a second light source is optional but always improves the measurement, because it makes it possible to use a value for the transmittance of the plant element that is independent of its water content.

The process comprises stages that consist in implementing an amplification of said alternating component of the light that is received by the photoreceptor tuned to the modulation frequency of the light sources, and a synchronous detection of the photoelectric signal to obtain at the output a signal that is proportional to the optical power that has passed through the plant element. The method for processing the photoelectric signal that is obtained can be analog or digital.

If an analog chain (passband filter and synchronous detection) is used, a continuous signal that is proportional to the optical power that has passed through the plant element at the output is obtained. The narrow-band filter makes it possible to reduce the signals of noise outside of the passband of the relevant signal and to adjust the phase shift of the pre-amplification chain so that the photoelectric signal and the reference signal are in phase (or in phase opposition) at the input of the synchronous detector. The latter implements the rectification of the alternating signal to provide a continuous signal.

If a digital-to-analog converter (DAC) combined with a digital signal processor is used, a digital signal that is proportional to the component of the modulated optical power that has passed through the plant element and a digital value that is proportional to the effective value of this photoelectric signal are obtained at the output. In this latter case, after having implemented the amplification of said alternating component of the light that is received by the photoreceptor, the analog signal is converted into a digital signal, and it is processed by taking for reference a clock signal that is produced by a digital signal processor DSP, coherent with the modulation signal of the light sources.

According to another preferred characteristic of the claimed process, the temperature at the junction of the first light source, as well as preferably that of the photoreceptor, are kept at a constant value, corresponding perfectly to the absorption line of water in the plant. Also preferably, the polarization voltage of the photoreceptor is kept constant during the measurement.

According to an advantageous characteristic of the invention, the light that is emitted by the light source(s) passes through an optical assembly that can ensure a broad uniform illumination of the plant element. It can pass through a set of prisms whose reflective surface forms a 45-degree angle with the incident ray and the lenses, placed on both sides of the plant element. For example, it passes through a first lens and a first prism upstream from the plant element, and then downstream from the latter, a second prism and a second lens for focusing the light that is transmitted on the photoreceptor.

According to a particularly advantageous variant embodiment of the fact of the miniaturization that it makes possible without loss of precision of the image, the light that is emitted by the light source(s) passes through two Fresnel prisms whose reflective surface comprises a number of facets forming a 45-degree angle with the incident ray, whereby said prisms are placed on both sides of the plant element.

In one particular embodiment of the process according to the invention, a probe is used that is carried by a moving element that comprises two jaws that are separated by a gap, supporting, opposite one, the light source(s) and, opposite the other, the photoreceptor, and said jaws are placed on both sides of the plant element prior to taking a measurement. In this case, preferably, during the placement of jaws on both sides of the plant element, said jaws are opened, and then they are closed until they reach a stop for adjusting the opening of the latter in measuring position.

Advantageously, when successive measurements of the optical transmission coefficient of a plant element are taken using said probe that is carried by said moving element, the latter is retracted into an inner housing of the apparatus between the taking of two measurements. According to an advantageous embodiment of the process that is the object of the invention, the plant element is permanently kept in a non-restrictive position by immobilization of a portion of the plant that carries said element, such as the one that is accessible to the moving element that bears the probe.

The process according to the invention can also comprise one or more operations that consist in carrying out the acquisition of data relative to the climatic and/or geographic environment of said plant element. Finally, this process can comprise at least one of the following operations, managed by a local automatic system or controlled remotely:
Initiating and implementing the taking of measurements,
Controlling electronic and mechanical functions,
Management of communications,
Acquisition, safeguarding, and transfer of data,
Supplying energy by an independent source.

As indicated above, it is possible to carry out several successive measurements of the same plant element so as to monitor the changes in the water content of said element. It is also considered to carry out a number of measurements at different points of a plant cover that occupies a more or less extended zone. These measurements can be carried out by an operator who is equipped with a portable device according to the invention and who moves from one point to another of the zone to be studied. They can also be carried out using several apparatuses in automatic mode that are installed permanently at different points of the plant cover that is studied. The application of a device for determining the hydration rate of a plant element in its natural environment as it was described above, or an apparatus for monitoring the hydration rate of a plant element in its natural environment that is also described above, is thus claimed in the evaluation and tracking over time of the hydration state of a plant cover.

The application of a process for determining the hydration rate of a plant element by measuring the optical transmission coefficient as described above is also claimed in the evaluation and in the tracking over time of the hydration state of a plant cover. This assumes that the stages that constitute said process can be repeated at a selected interval of time, and preferably at different points of the plant zone that is to be monitored, which is made possible according to this invention by the combination of means that are implemented and that are able to be organized in a network and controlled remotely.

The repetition of a measurement on the same sample at different times makes it possible to establish, on the scale of a plant cycle or a season, a specific and significant dynamic profile of the leaf hydric state. It makes it possible to eliminate the noise that is linked to the heterogeneity of state that can be observed at a given moment between two leaves or even between two adjacent plants. Finally, it makes it possible to demonstrate the hydric state variations of low importance that would not be perceptible within the context of sound effects of a destructive measurement.

BRIEF DESCRIPTION OF THE DRAWING FIGURES

This invention will be better understood using examples and figures that illustrate a particular embodiment without limiting its scope.

DESCRIPTION OF THE INVENTION

Example 1

Device for Photometric Measurement of a Plant Element

Figure 1:
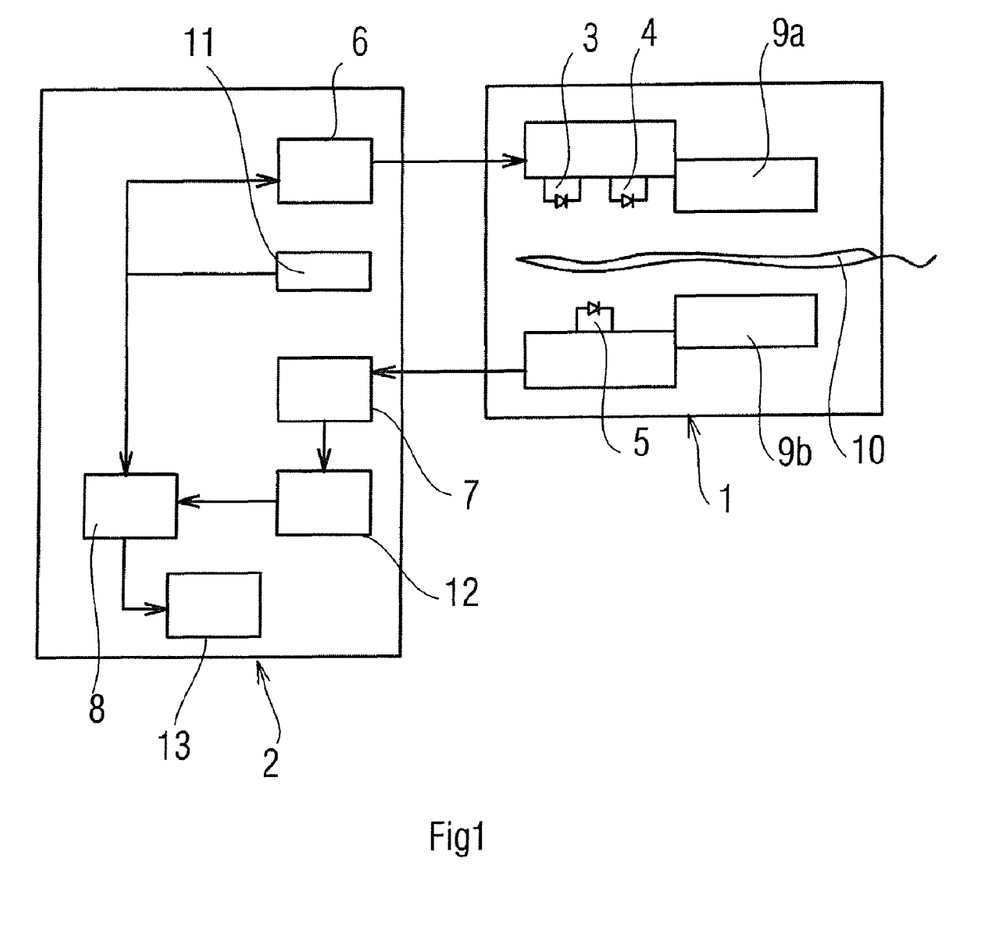
FIG. 1 is a functional diagram of the device for photometric measurement of a plant element according to the invention that comprises a probe and a measuring box.

The device for determining the hydration rate of a plant element in its natural environment comprises here the optoelectronic probe 1, combined with the measuring box 2. The probe 1 comprises two LEDs that emit a narrow-band spectrum: LED 3 that emits at the wavelength of 1,940 nm that corresponds to a band of high water absorption, as well as LED 4, emitting at 1,300 nm and slightly absorbed by water. It also comprises the photodiode 5 that is coupled to its amplifier, whose spectral response corresponds to the emission bands of the two LEDs. The box 2 contains a primary electronic card that integrates the bulk of the electronics implemented. The box 2 and the probe 1 form two separate elements that are connected physically by a cable or a ribbon cable. The adjustment of the central emission wavelength of LED 3 is carried out by the temperature regulator 9a of the junction. LED 4 that is centered on 1,300 nm makes possible a calibration of the optical transmission measurement of the sample by determination of an attenuation of the independent signal of the water content of the sample. This LED is not regulated in temperature.

To eliminate the very strong substantial component of the photoelectric current of the photodiode due to the ambient illumination, the mean power emitted by the LEDs is modulated at a determined frequency that is imposed by the clock 11. Only this alternative component of the photoelectric current that contains the information is then processed by the detection chain.

The photodiode 5 is regulated in temperature by the regulator 9b that is integrated in the box of the photodiode. The technology of the semi-conductor that is necessary for providing the desired spectral response has the consequence that this photodiode has a significant darkness current. To reduce this darkness current, two techniques are implemented:
A polarization at 0 V, imposed by a transimpedance circuit (not shown);
A regulation at a lower temperature than the ambient temperature. The photodiode 5 is characterized by very high linearity dynamics. As a result, the low amplitude of the alternating current that contains the information is superposed, with neither deformation nor compression that is significant to the very substantial component that is generated by the ambient light. It is thereby necessary that the transimpedance circuit that keeps constant the polarization voltage of the photodiode remains a linear regime. This substantial current degrades the photoelectric signal-to-noise ratio by generating a shot noise current, whose quadratic spectral density is constant (source of white noise). In order to optimize the signal-to-noise ratio, a selective amplification (by the amplifier 7) is carried out, whereby said amplification is tuned to the modulation frequency, which prevents the input of the synchronous detector 8 from being overloaded with noise. The amplifier 12 whose voltage gain can be programmed to adjust the dynamics of the synchronous detector 8 is introduced. The time constant of the passband filter 13 at the output of the synchronous detection imposes the equivalent passband of noise of the chain. The synchronous detection implements the rectification of the alternating signal whose mean value is proportional to the amplitude of the photoelectric signal. It is this mean component that is measured. The analog chain of the measurement is described by FIG. 1. The electronic components that are implemented are standard components that are available and easily accessible on the market. Replacement solutions can be considered provided that the expected functionality of the component is preserved.

Figure 1A:
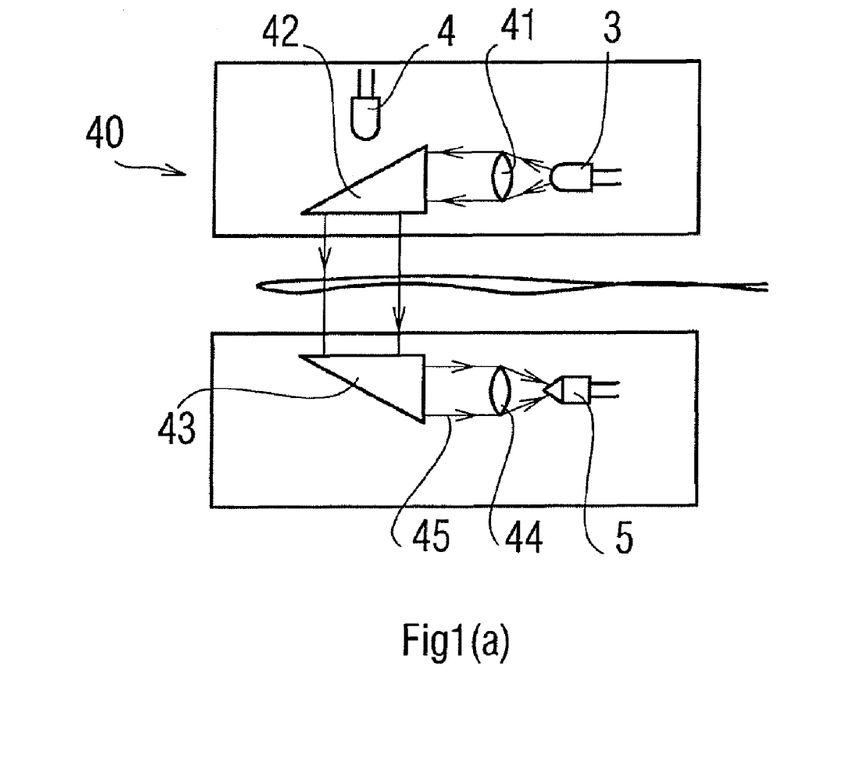
FIG. 1a diagrammatically represents an optical assembly for broad illumination of a plant element, comprising a set of lenses and flat prisms.
Figure 1B:
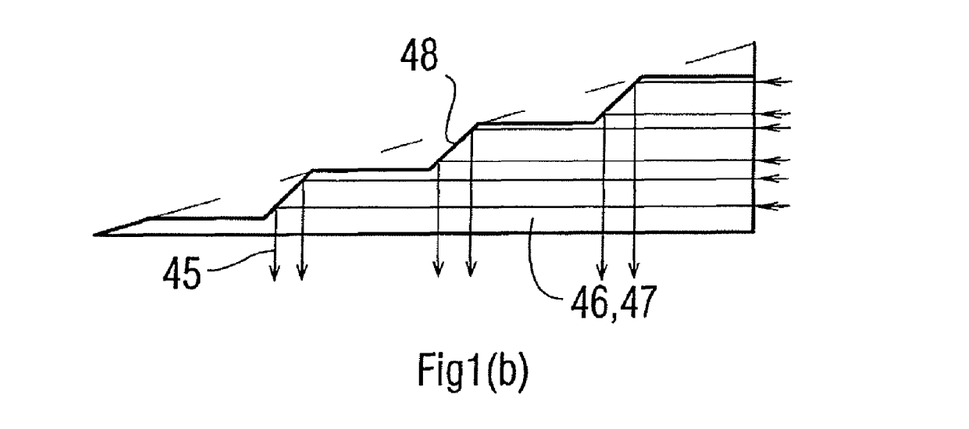
FIG. 1b diagrammatically represents an optical assembly for the broad illumination of a plant element, comprising two Fresnel prisms.

The probe 1 can be equipped with the optical assembly 40, shown in FIG. 1a. The light is emitted by the first LED 3 at 1,940 nm and by the LED with calibration 4 at 1,300 nm. The light passes through the first lens 41 and then the flat prism 42. The uniform beam at the output of the first prism 42 then irradiates the plant element 10 over a broad zone. The transmitted light is received by the second flat prism 43 and then focused by the second lens 44 on the photoreceptor 5. In an alternative way that has advantages from the standpoint of miniaturization possibilities, the flat prisms 42, 43 and the lenses 41, 44 are replaced by two Fresnel prisms 46, 47, equipped with a number of facets 48, arranged at 45 degrees relative to the incident beam and in "stair steps," deflecting the light beam according to the same principle as the Fresnel lenses.

In the two cases, a uniform and broad illumination of the plant element 10 (the optical travel of the beam 45 is shown in fine lines) is obtained. The assembly 40 has a minimum space requirement and can easily be integrated into a compact device, which allows its miniaturization by remaining compatible with an excellent precision of measurement.

Example 2

Device with a Moving Element Supporting the Probe

Figure 3:
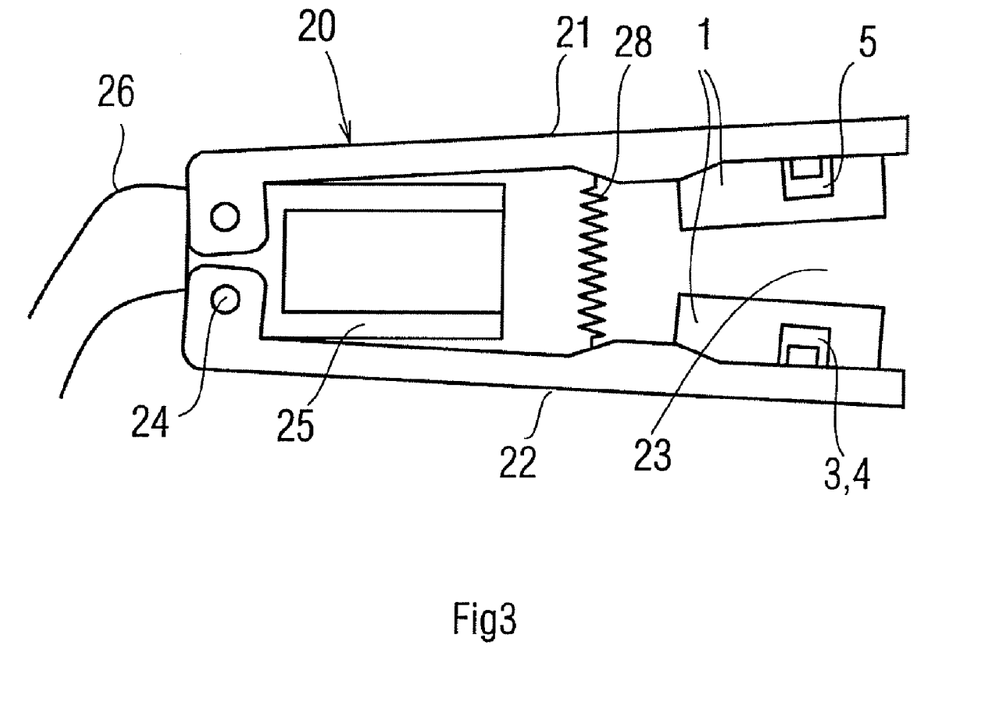
FIG. 3 shows a moving element that carries a probe, with articulated jaws that are activated by a draw spring.

In FIG. 3, the probe 1 of the device that is described in Example 1 is carried by the moving element 20, comprises the two jaws 21 and 22 that move around the joint 24 and are separated by the gap 23. This element makes it possible:

To collect the detection electronics of the photometer;
To ensure the positioning and the holding of LEDs 3 and 4 and of the photodiode 5 in the measurement configuration;
To ensure, by a suitable ergonomy, the production and the repetition of transmittance measurements in vivo on plant samples.

The implementation of the moving element 20 (opening/closing) can be carried out automatically or manually. The neutral position of the jaws 21, 22 is ensured by the action of springs 28 and varies according to the automatic or manual mode. In automatic mode, the neutral position is the closed position that is maintained by draw springs; in manual mode, the neutral position is the open position that is ensured by flat springs. The measuring electronics is mounted integrally at the two ends of the jaws 21, 22 directly facing one another by tightening said jaws. The photodiode 5 is located on the upper jaw 21 so as to limit the direct solar illumination. The LEDs 3, 4 are located on the lower jaw 22, emitting their light flow upward. The elements 3, 4, 5 for emission and detection can be protected from the insertion of foreign bodies (dust, water, . . . ) by two protective plates that are transparent to the wavelengths that are considered (not shown). The gap between the two jaws 21, 22 is 15 mm and constitutes the zone for inserting the sample 10.

The electrical cabling of the emission and detection elements is each integrated for its part in the support jaw. The gap between the LEDs 3, 4 and the photodiode 5 is constant, or 5 mm (edge to edge of the components); the adjustable stop 25 that is placed at the origin of the moving element 20 makes possible good positioning facing these elements. The illuminated surface (at the level of the sample) is on the order of 2 $cm^2$ and can be reduced by circular opacification, on the one hand, of the protective plate. The addition of removable protective skirts made of flexible plastic makes it possible to limit the contributions of the outside illumination. The sample 10 is engaged without compressive contact between the two jaws 21, 22. The optical components are at a fixed, determined distance from one another during the measurements.

Example 3

Apparatus for Tracking the State of Hydration of a Plant Cover

Figure 2:
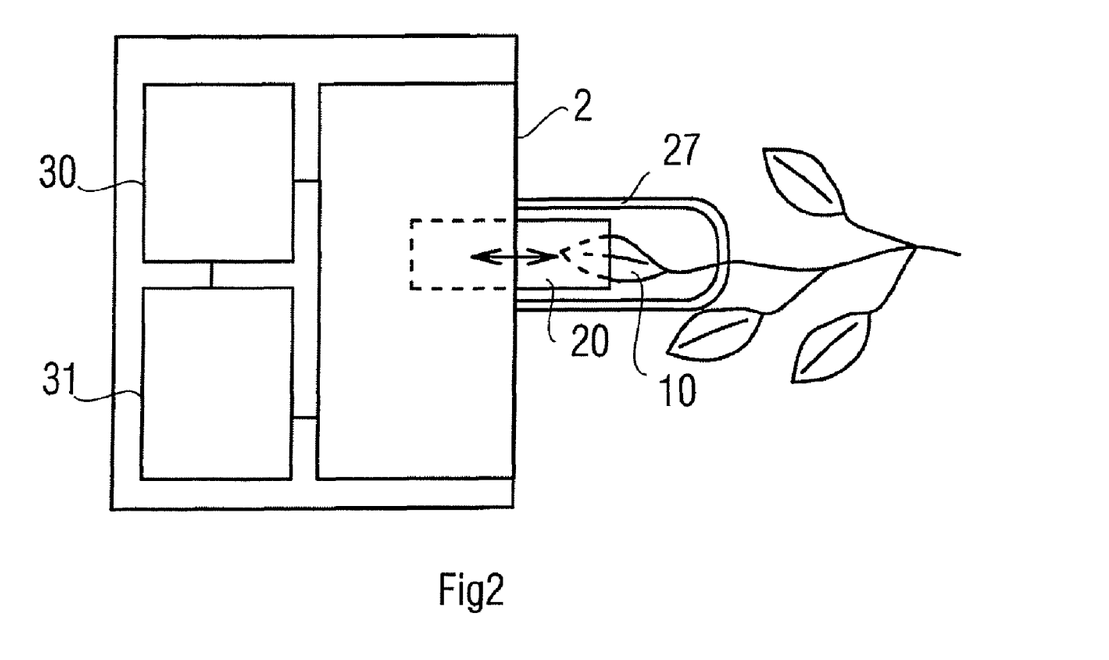
FIG. 2 is a functional diagram of an apparatus for evaluation and tracking of the hydration state of a plant cover according to the invention.

The apparatus that is shown in FIG. 2 is produced with a device and a moving element as described in Examples 1 and 2 respectively. The apparatus that is presented here has an automatic operating mode. It comprises means for holding the plant sample in a non-restrictive position, and communication means 31 with a control module 30, connected by the cabling 26.

3.1) Holding the Sample

The portico 27 consists of a circular rod with variable geometry according to the morphology of the sample (leaf surface, length/width ratio, . . . ) and of the plant that carries it (woody or non-woody plant). It has a standard ending, for example two parallel pins, making possible its insertion into the body of the apparatus. Fastening straps that make it possible to attach the plant in a way that does not alter or destroy it consist of:

One or two points for fastening to the portico, adjustable in position by sliding and immobilization by tightening screws;
Docking point of the plant (branches or stems).

The number of straps varies according to the plant (type of plant, characteristics of the leaves, . . . ) and the environmental conditions, in particular the wind.

3.2) The System Environment

Figure 4:
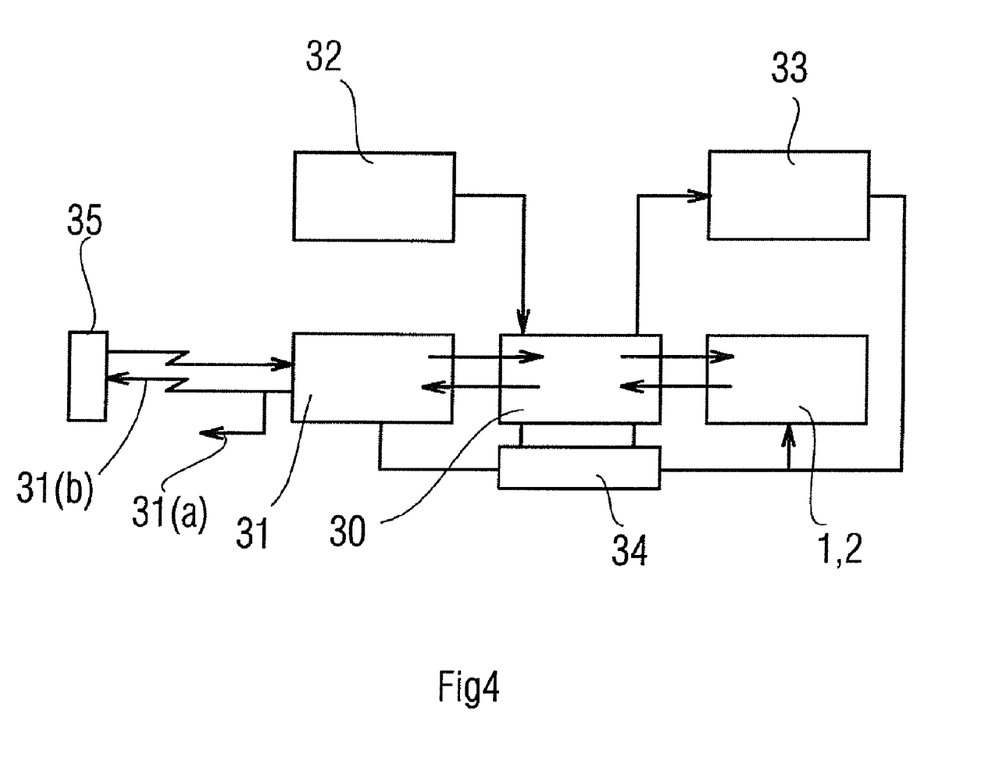
FIG. 4 is a flow chart of an apparatus according to the invention, illustrating a process of operation according to an automated mode.

The system environment shown in FIG. 4 makes possible stationary implantation in the natural environment, remote management, and automation of the measuring cycle, in particular the auto-calibration of the measuring electronics, the slaving of the position of the probe to the sample during measurement, and the remote transmission of the measurement once the measurement is taken. It constitutes a central unit that is the master assembly including in particular the motherboard and the batteries and can be located locally in the apparatus or partially remotely, according to a structure that is suitable for the operation of the apparatus that is the object of the invention and designed according to the rules of the art that are known to one skilled in the art.

3.2.1) The Control Module or the Microcontroller

This module 30 has for its functions:

To control individually the different modules that are involved in the implementation of the measuring cycles and to coordinate their actions;
To manage the automatic programming of the measurements;
To optimize the energy management of the probe 1;
To acquire, process, store and then restore the different components of the measurement;

To ensure the integrity of the measuring chain.

It assumes the shape of an electronic card with a microcontroller that is housed in the central unit, which is designed in a reduced-area surface logic.

3.2.2) The "Interface Communication" Module

This is an assembly 31 that consists of two sub-modules dedicated to the local communication 31(a) and to the remote communication 31(b). They have as their functions:

To receive and manage orders for initiating measurement cycles originating from a local user (manual mode) or a remote requestor (automatic mode);

To restore to this local user or to the remote requestor the result of the measurement, by display or transmission;

To allow the parameterization of the device.

The submodule for remote communication 31(b) is a GSM-type wireless communication module on the communication card. It is equipped with an outside antenna positioned on the upper block of the central unit. The mode for initiating the selected measurement cycle conditions the physiognomy of the GSM link:

In exclusive automatic mode, the microcontroller automatically initiates the measuring cycles on programmed schedules: the GSM probe is used to transmit the result of the measurement to the GSM administrator.

In exclusive non-automatic mode, the initiation of a measuring cycle passes by sending an SMS from the GSM user to the GSM probe. Upon receiving the SMS, the GSM-probe sensor transmits the information to the microcontroller that initiates the measurement, and then transmits the result of the measurement to the GSM administrator.

In mixed mode, the activations are carried out simultaneously by the user and by the device (programming).

The two latter modes imply that the GSM probe is on permanent watch.

3.2.3) The "Supply" Module

This module 34 has as its functions:

To ensure the electrical supply that is suitable and necessary to the good operation of the microcontroller 30 and the measuring device in the case of the manual implementation of the probe 1, as well as modules 31 for communication and automatism of the moving element 20 in the case of an automatic implementation of the device;

To ensure, in this second case, an autonomy of the device for a duration that is compatible with the needs that are expressed by the users of the terrain.

It consists of an internal power supply such as batteries or power cells for manual and automatic modes, completed by an external solar-type supply with a photovoltaic panel for the automatic mode.

3.2.4) The "Probe Automatism" Module

This module 33 has as its functions:

To make possible, upon initiation of a measuring cycle, the temporary positioning of the probe 1 on the sample 10 for the measurement and its withdrawal once the measurement is taken;

To shelter the probe 1 from external attacks (dust, radiation, rain, . . . ) outside of the measurement phases.

It comprises a specific housing in the receiving base, as well as an automatic device for deployment/redeployment of the moving element 20. The deployment/redeployment system of the moving element 20 consists of a slaving to a linear movement. It is carried out by means of a linear stepper motor. The motor is integral with the element 20 (at the rear surface), and the front end of the screw is attached to the receiving base. The motor is controlled by the microcontroller 30.

3.2.5) The "Meteo Environment Parameters" Module

This is an offloaded module 32 that has as its functions:

To characterize the meteorological environment that surrounds the spectral measurement by recording, for example, cumulative precipitation over the last 24 hours and a time-stamping of the last rain event; the ambient temperature under shelter at the time of measurement; the relative humidity of the air under shelter at the time of measurement; the average speed and the direction of the wind at the time of measurement;

To send in time and hour the data back to the microcontroller 30.

Example 4

Execution of the Measurements—Process

In a manual configuration, the measurement is taken by an operator that is present on the site. The operator turns on the device, starts up the testing phase (input electrical voltage and transmit/receive link balance sheet) and implements a vacuum measurement (without sample). The moving element 20 is then positioned manually on the leaf in test 10 to carry out the transmittance measurement. The microcontroller 30 then initiates the calculation of the transmittance and compiles the information to be sent (the parameters of the device) and the measurements of transmittance, locally and/or remotely. The device is then turned off.

In an automatic configuration, the measurement is taken by an apparatus as described above, according to an operating mode that uses the modules of FIG. 4. Outside of the measurement phases, the apparatus that is installed close to the monitored plant is in watch position. Its activation and the initiation of a measurement are carried out upon receiving a remote order or by programmed automatic initiation. The information is communicated to the microcontroller 30 that in its turn simultaneously controls the "probe automatism" module 33 and the photometric device 1, 2. The chronology of the actions is as follows:

Testing phase of the integrity of the photometric device (input electrical voltage and transmit/receive link balance sheet);

Execution of a vacuum measurement in neutral position of the jaws 21, 22;

Translation of the moving element 20 and positioning of the probe 1 on the sample 10;

Execution of the leaf transmittance measurement;

Control for return of the moving element 20.

The microcontroller module 30 then initiates the calculation of the transmittance and then compiles the data to be sent (meteo data, parameters of the probe, and transmittance measurements). Sending is done remotely to a receiving center 35. At the end of the cycle, the apparatus returns to its watch state.

The invention claimed is:

1. A device for determining the rate of hydration of a plant element (10) in the plant's natural environment, said device comprising:

an optoelectronic probe (1) to take a measurement of an optical transmission coefficient of the plant element (10), said probe comprising i) a first light source (3) that emits light limited to a narrow-band spectrum at a first wavelength corresponding to a band of high water absorption, ii) a photoreceptor (5) having a spectral response corresponding to the first wavelength narrow-band spectrum light emitted by the first light source, the light emitted by the first light source having a mean optical power, and iii) a space between the first light source and the photoreceptor, the space sized a) for allowing placement of a plant element (10) between the first light source and the photoreceptor such that the plant element (10) is sampled in the plant's natural environment, b) so that the light emitted by the first light source passes through the plant element (10) and, after absorption by water contained in the plant element (10), the light emitted by the first light source leaves the plant element corresponding to an absorption spectral line of the water contained in the plant element, and c) to allow both the light emitted by the first light source leaving the plant element (10) corresponding to the absorption spectral line of the water and ambient light to be received by the photoreceptor; and a measuring box (2) connected to the probe, the measuring box (2) housing i) a modulator (6) arranged to modulate the mean optical power of the light emitted by the first light source (3) by modulating the first light source (3) at a determined imposed frequency and thereby creating an alternating light component illuminating the plant element (10) at the first wavelength, and ii) a synchronous detector (8) arranged for synchronous detection and rectification of the alternating light component received by the photoreceptor at the absorption spectral line of the water, the wherein relevant information relating to a hydration rate in the plant element (10) is indicated by the measured alternating light component emitted by the first light source and leaving the plant element corresponding to the absorption spectral line of the water contained in the plant element (10) and the ambient light received by the photoreceptor is eliminated from the detection.

2. The device of claim 1, wherein, the optoelectronic probe (1) further comprises a second light source (4) that emits light limited to a narrow-band spectrum light at a second wavelength corresponding to a band of low water absorption, the second wavelength being close to the first wavelength, the spectral response of the photoreceptor (5) further corresponds to the narrow-band spectrum light emitted by the first and second light sources, after passing through the plant element (10), the second light source (4) being configured for calibrating the first light source (3) independent of a water content of the plant element (10), and the modulator (6) arranged to modulate the mean optical power of the light emitted by the first and second light sources (3, 4) by modulating the first and second light sources (3, 4) at the determined imposed frequency as alternating light components.

3. The device of claim 2, wherein, said first light source is an LED emitting at a wavelength of one of 1,940 nm and 1,450 nm, and said second light source is an LED emitting at a wavelength of 1,300 nm.

4. The device of claim 2, further comprising an amplifier (7) at an output of the photoreceptor (5), tuned to the determined imposed frequency modulating the first and second light sources, for amplification of the measured light at the absorption spectral line of the water contained in the plant element (10).

5. The device of claim 4, further comprising a thermal regulator (9a, 9b) to keep constant a temperature of a junction of the first light source (3) and a temperature of the photoreceptor (5).

6. The device of claim 5, wherein the first and second light sources (3, 4) are one of electroluminescent diodes, single-strip laser diodes, and surface-emission laser diodes.

7. The device of claim 6, where the first and second light sources (3, 4) are positioned relative to an optical assembly (40) to provide a broad uniform illumination of the plant element (10) in the space.

8. The device of claim 4, further comprising:

a moving element (20) carrying the probe (1), the moving element (20) comprising two jaws (21, 22), a first of the two jaws supporting the first and second light sources (3, 4) opposite a second of the jaws supporting the photoreceptor (5), wherein said two jaws are separated by the space (23) such that the first and second light sources (3, 4) and the photoreceptor (5) are placed on both sides of the plant element (10) during taking of a measurement.

9. The device of claim 8, further comprising a holding element (27) for holding the plant element (10) in a non-restrictive position within the space between the first and second light sources and the photoreceptor; and a communication element (31) for communicating with a control element (30).

10. The device of claim 9, further comprising:

an internal housing for protection of the moving element (20); and an automatic mechanism controlling i) the moving element for moving the moving element up to the plant element (10) during the taking of a measurement, and ii) movement of the two jaws (21, 22).

11. A method for determining a hydration rate of a plant element (10) in the plant's natural environment by measuring the optical transmission coefficient using an optoelectronic probe (2), the method comprising the steps of:

emitting light from a first light source (3) that emits a narrow-band spectrum light corresponding to a band of high water absorption;

modulating a mean optical power of the light emitted by the first light source (3) at a determined imposed frequency to obtain an alternating component of the light at the spectrum corresponding to the band of high water absorption, and irradiating the plant element (10) with the obtained alternating component of the light;

receiving said alternating component of the light that has passed through the plant element (10) on a photoreceptor (5); and carrying out a synchronous detection of the photoelectric signal from the photoreceptor (5) to determine a hydration rate of a plant element (10), the determination based on the alternating component of the light at the spectrum corresponding to the band of high water absorption with ambient light received by the photoreceptor being eliminated from the determination.

12. The method of claim 11, comprising the further steps of:

emitting light from a second light source (4) that emits a narrow-band spectrum light corresponding to a band of low water absorption; and modulating both the first and second light sources at a determined imposed frequency to obtain the alternating component of the light at the spectrum corresponding to the band of high water absorption.

13. The process of claim 12, comprising the further step of amplification of said alternating component of the light that is received by the photoreceptor (5) to obtain an amplified output signal that is proportional to an optical power that has passed through the plant element (10).

14. The process of claim 12, comprising the further step of regulating a temperature of a junction of the first light source (3) to be constant and regulating a temperature of the photoreceptor (5) to be constant.

15. The process of claim 12, wherein the alternating light component emitted by the first and second light sources passes through an optical assembly (40) to ensure a broad uniform illumination of the plant element (10).

16. The process of claim 12, comprising the further step of wherein,
    successive measurements of an optical transmission coefficient of a plant element (10) are taken, and
    a probe (2) containing the first and second light sources and the photoreceptor is i) carried by a moving element (20), and ii) retracted into an internal housing between taking measurements.

17. The process of claim 16, comprising the further step of keeping the plant element (10) permanently in a non-restrictive position by immobilization of a portion of the plant that carries said plant element such that the plant element is accessible to the moving element (20) that carries the probe (2).

18. The process of claim 12, comprising the further step of implementing an acquisition of data relative to the climatic and/or geographic environment of said plant element.

19. The process of claim 11, comprising the further step of, in the emitting light step, emitting light from a second source (4) that emits at a wavelength close to the first source (3) and slightly absorbed by water for allowing the calibration of the optical transmittance measurement.

20. The process of claim 19, wherein,
    said first light source is an LED emitting at a wavelength of one of 1,940 nm and 1,450 nm, and
    said second light source is an LED emitting at a wavelength of 1,300 nm.

* * * * *